US011651499B2

(12) United States Patent
Wang et al.

(10) Patent No.: US 11,651,499 B2
(45) Date of Patent: May 16, 2023

(54) REDUCING STRUCTURAL REDUNDANCY IN AUTOMATIC IMAGE SEGMENTATION

(71) Applicant: INTERNATIONAL BUSINESS MACHINES CORPORATION, Armonk, NY (US)

(72) Inventors: Hongzhi Wang, Santa Bruno, CA (US); Tanveer Syeda-Mahmood, Cupertino, CA (US)

(73) Assignee: International Business Machines Corporation, Armonk, NY (US)

(*) Notice: Subject to any disclaimer, the term of this patent is extended or adjusted under 35 U.S.C. 154(b) by 246 days.

(21) Appl. No.: 16/948,420

(22) Filed: Sep. 17, 2020

(65) Prior Publication Data

US 2022/0084209 A1  Mar. 17, 2022

(51) Int. Cl.
*G06T 7/143* (2017.01)
*G06T 7/00* (2017.01)

(52) U.S. Cl.
CPC ............ *G06T 7/143* (2017.01); *G06T 7/0012* (2013.01); *G06T 2200/24* (2013.01);
(Continued)

(58) Field of Classification Search
None
See application file for complete search history.

(56) References Cited

U.S. PATENT DOCUMENTS 916,046 A  3/1909  Smith
8,135,202 B2  3/2012  Cosatto
(Continued)

FOREIGN PATENT DOCUMENTS

CN  110377779 A  10/2019
DE  102010026966 A1  1/2012
(Continued)

OTHER PUBLICATIONS

Dutt Jain, et al., "Active Image Segmentation Propagation," 2016 IEEE Conference on Computer Vision and Pattern Recognition (CVPR), Jun. 27-30, 2016, pp. 2864-2873, IEEE, Las Vegas, NV, USA, DOI: 10.1109/CVPR.2016.313, Retrieved from the Internet: <URL: https://ieeexplore.ieee.org/document/7780682>.
(Continued)

*Primary Examiner* — Vu Le
*Assistant Examiner* — Courtney Joan Nelson
(74) *Attorney, Agent, or Firm* — Steven M. Bouknight

(57) ABSTRACT

A method for automatically training and applying automatic segmentation in digital image processing is provided. The method may include, in response to receiving a plurality of digital images wherein each digital image associated with the plurality of digital images comprises only one annotated structure out of a plurality of structures included in each digital image, applying a predictive algorithm to each digital image that determines a predicted probability of each annotation in each digital image, determines a predicted background for each digital image, and merges the predicted probability of each annotation with the predicted background in each digital image. The method may further include, in response to applying the predictive algorithm, using the received plurality of digital images to train and apply an application for automatically segmenting unlabeled digital images.

20 Claims, 7 Drawing Sheets

(52) U.S. Cl.
CPC ............... *G06T 2207/10116* (2013.01); *G06T 2207/20076* (2013.01); *G06T 2207/20081* (2013.01)

(56) References Cited

U.S. PATENT DOCUMENTS

| | | | |
|---|---|---|---|
| 9,014,485 B2 | 4/2015 | Moehrle | |
| 9,196,046 B2 | 11/2015 | Meyer | |
| 10,127,662 B1* | 11/2018 | Reicher | G06T 7/30 |
| 10,275,690 B2 | 4/2019 | Chen | |
| 10,430,949 B1* | 10/2019 | Wang | G06T 7/0012 |
| 10,595,727 B2* | 3/2020 | Lu | A61B 5/0044 |
| 10,606,982 B2 | 3/2020 | Guo | |
| 11,030,747 B1 | 6/2021 | Feng | |
| 2008/0136838 A1 | 6/2008 | Goede | |
| 2016/0119388 A1* | 4/2016 | Sitrick | G06F 40/169 |
| | | | 715/753 |
| 2016/0314246 A1 | 10/2016 | Roberge | |
| 2019/0030371 A1 | 1/2019 | Han | |
| 2019/0156204 A1 | 5/2019 | Bresch | |
| 2019/0205606 A1* | 7/2019 | Zhou | G06N 3/0445 |
| 2019/0220701 A1 | 7/2019 | Novak | |
| 2019/0251694 A1* | 8/2019 | Han | G06T 7/11 |
| 2019/0259494 A1 | 8/2019 | Merlijn | |
| 2019/0347524 A1* | 11/2019 | Znamenskiy | G06V 20/698 |
| 2019/0355128 A1 | 11/2019 | Kristen | |
| 2020/0380312 A1 | 12/2020 | Khan | |
| 2020/0380675 A1* | 12/2020 | Golden | G16H 50/70 |
| 2021/0256420 A1 | 8/2021 | Oren | |
| 2021/0272288 A1 | 9/2021 | Takahashi | |
| 2021/0303930 A1 | 9/2021 | Wang | |
| 2021/0303931 A1 | 9/2021 | Wang | |

FOREIGN PATENT DOCUMENTS

| | | |
|---|---|---|
| WO | 2013160382 A1 | 10/2013 |
| WO | 2018189550 A1 | 10/2018 |
| WO | 2020031243 A1 | 2/2020 |

OTHER PUBLICATIONS

Francis, et al., "Neural Network Segmentation of Cell Ultrastructure Using Incomplete Annotation," 2020 IEEE 17th International Symposium on Biomedical Imaging (ISBI), Apr. 3-7, 2020 [accessed on Sep. 11, 2020], pp. 1183-1187, Iowa City, IA, USA, DOI10.1109/ISBI45749.2020.9098739, Retrieved from the Internet: <URL: https://ieeexplore.ieee.org/document/9098739>.

Iglesias, et al., "Multi-Atlas Segmentation of Biomedical Images: A Survey," Elsevier, Jun. 12, 2015, 20 pages, DOI: .org/10.1016/j.media.2015.06.012, Retrieved from the Internet: <URL: https://www.sciencedirect.com/science/article/abs/pii/S1361841515000997?via%3Dihub>.

Lin, et al., "Focal Loss for Dense Object Detection," IEEE Transactions on Pattern Analysis and Machine Intelligence, Feb. 1, 2020, pp. 318-327, vol. 42, Issue 2, IEEE, DOI: 10.1109/TPAMI.2018.2858826, Retrieved from the Internet: <URL: https://ieeexplore.ieee.org/stamp/stamp.jsp?tp=&arnumber=8417976>.

Mell, et al., "The NIST Definition of Cloud Computing", National Institute of Standards and Technology, Special Publication 800-145, Sep. 2011, 7 pages.

Oktay, et al., "Anatomically Constrained Neural Networks (ACNNS): Application to Cardiac Image Enhancement and Segmentation," IEEE Transactions on Medical Imaging, Feb. 2018, pp. 384-395, vol. 37, Issue 2, IEEE, DOI: 10.1109/TMI.2017.2743464, retrieved from the Internet: <URL: https://ieeexplore.ieee.org/document/8051114>.

Papandreou, et al., "Weakly-and Semi-Supervised Learning of a Deep Convolutional Network for Semantic Image Segmentation," IEEE Computer Society, 2015 IEEE International Conference on Computer Vision, DOI 10.1109/ICCV.2015.20, pp. 1742-1750.

Petit, et al., "Handling Missing Annotations for Semantic Segmentation with Deep Convnets," MICCAI 2018 Workshop DLMIA, 2018, 9 pages, Springer, Genade, ES, Retrieved from the Internet: <URL: https://hal.archives-ouvertes.fr/hal-02471187/file/handling_missing_annotations_DLMIA_MICCAI_2018%281%29.pdf>.

Top, et al., "Active Learning for Interactive 3D Image Segmentation," Medical Image Computing and Computer-Assisted Intervention—MICCAI 2011, 2011, pp. 603-610, Springer-Verlag, Berlin, Heidelberg, DE, Retrieved from the Internet: <https://link.springer.com/chapter/10.1007/978-3-642-23626-6_74>.

Van Harten, et al., "Exploiting Clinically Available Delineations for CNN-based Segmentation in Radiotherapy Treatment Planning," SPIE Medical Imaging 2020, Nov. 12, 2019, 7 pages, arXiv: 1911.04967v1, Retrieved from the Internet: <URL: https://arxiv.org/pdf/1911.04967.pdf>.

Wang, et al., "ChestX-ray8: Hospital-scale Chest X-ray Database and Benchmarks on Weakly-Supervised Classification and Localization of Common Thorax Diseases," 2017 IEEE Conference on Computer Vision and Pattern Recognition (CVPR), July 21-26, 2017 [accessed on Sep. 11, 2020], pp. 3462-3471, IEEE, Honolulu, HI, USA, DOI: 10.1109/CVPR.2017.369, Retrieved from the Internet: <URL: https://ieeexplore.ieee.org/document/8099852>.

Wang, et al., "Model Training Using Fully and Partially-Annotated Images," Application and Drawings, Filed on Mar. 31, 2020, 27 pages, Related U.S. Appl. No. 16/836,106.

Wang, et al., "Model Training Using Partially-Annotated Images," Application and Drawings, Filed on Mar. 31, 2020, 27 Pages, Related U.S. Appl. No. 16/836,115.

Wang, et al.,"Rapid Annotation of 3D Medical Imaging Datasets Using Registration-Based Interpolation and Adaptive Slice Selection," 2018 IEEE 15th International Symposium on Biomedical Imaging (ISBI 2018), Apr. 4-7, 2018 [accessed on Sep. 11, 2020], pp. 1340-1343, IEEE, Washington, DC, USA, DOI: 10.1109/ISBI.2018.8363819, retrieved from the Internet: <URL: https://ieeexplore.ieee.org/document/8363819>.

Anfinsen, "Principles that Govern the Folding of Protein Chains," Science, Jul. 20, 1973, pp. 223-230, vol. 181, No. 4096.

Çiçek, et al., "3D U-Net: Learning Dense Volumetric Segmentation from Sparse Annotation," Computer Vision and Pattern Recognition, Jun. 21, 2016, 8 pages, Cornell University, Retrieved from the Internet: <URL: https://arxiv.org/pdf/1606.06650.pdf>.

Cour, et al., "Learning from Partial Labels," Journal of Machine Learning Research, 2011, pp. 1501-1536, vol. 12.

Dehghany, et al., "A Spatial Model of Insulin-Granule Dynamics in Pancreatic beta-Cells," Traffic, 2015, pp. 797-813, John Wiley & Sons, Ltd, DOI: 10.1111/tra.12286.

Dice, "Measure of the Amount of Ecological Association Between Species," Ecology, Jul. 1945 [accessed on Jul. 8, 2020], 7 pages, vol. 26, No. 3, Wiley on behalf of the Ecological Society of America.

Ekman, et al., "Mesoscale imaging with cryo-light and x-rays: Larger than molecular machines, smaller than a cell," Biol Cell, 2017, 24 pages, DOI: 10.1111/boc.201600044.

Guerrero-Peña, et al., "A Weakly Supervised Method for Instance Segmentation of Biological Cells," arXiv:1908.09891, Aug. 26, 2019, 8 pages.

Kwon et al., "Uncertainty quantification using Bayesian neural networks in classification: Application to biomedical mage segmentation," Computational Statistics & Data Analysis, Jun. 10, 2019, 35 pages.

Litjens, et al., "A Survey on Deep Learning in Medical Image Analysis," arXiv:1702.05747v2, Jun. 4, 2017, 38 pages.

Lomanov, et al., "Cell Detection With Deep Convolutional Networks Trained With Minimal Annotations," 2019 IEEE 16th International Symposium on Biomedical Imaging (ISBI 2019), Apr. 8-11, 2019, pp. 943-947, Venice, IT.

Long, et al., "Fully Convolutional Networks for Semantic Segmentation," The IEEE Conference on Computer Vision and Pattern Recognition (CVPR), 2015, pp. 3431-3440.

Ronneberger, et al., "U-net:Convolutional Networks for Biomedical Image Segmentation," MICCAI 2015: Medical Image Computing and Computer-Assisted Intervention, May 18, 2015, 8 pages, arXiv:1505.

(56) References Cited

OTHER PUBLICATIONS

04597, Retrieved from the Internet: <URL:https://arxiv.org/pdf/1505.04597.pdf)%e5%92%8c%5bTiramisu%5d(https://arxiv.org/abs/1611.09326.pdf>.

Rorsman, et al., "Insulin granule dynamics in pancreatic beta cells," Diadetologia, 2003, pp. 1029-1045, vol. 46, DOI: 10.1007/s00125-003-1153-1.

United States Patent Office Action for U.S. Appl. No. 16/836,115 dated Sep. 16, 2021 (11 pages).

Verbeek, et al., "Scene Segmentation with Conditional Random Fields Learned from Partially Labeled Images," NIPS'07: Proceedings of the 20th International Conference on Neural Information Processing Systems, Dec. 2007, 8 pages, Retrieved from the Internet: <URL: https://dl.acm.org/doi/10.5555/2981562.2981757>.

IBM: List of IBM Patents or Patent Applications Treated as Related (Appendix P), Jul. 21, 2022, 2 pages.

Lin et al., "Focal loss for dense object detection," in ICCV, 2017, pp. 2980-2988.

United States Patent Office Action for U.S. Appl. No. 16/836,106 dated Mar. 21, 2022 (19 pages).

United States Patent Office Notice of Allowance for U.S. Appl. No. 16/836,115 dated May 18, 2022 (8 pages).

United States Patent Office Corrected Notice of Allowance for U.S. Appl. No. 16/836,115 dated Jun. 17, 2022 (2 pages).

\* cited by examiner

|  | RCO | SDA | trachea | lung | clavicle | average |
|---|---|---|---|---|---|---|
| RCO | - | 0.669 | 0.401 | 0.722 | 0.198 | 0.485 |
| SDA | 0.144 | - | 0.295 | 0.740 | 0.114 | 0.358 |
| trachea | 0.157 | 0.667 | - | 0.758 | 0.247 | 0.472 |
| lung | 0.324 | 0.760 | 0.571 | - | 0.270 | 0.505 |
| clavicle | 0.158 | 0.624 | 0.451 | 0.727 | - | 0.497 |

Table 1. Segmentation performance (mean dice similarity coefficient) produced by shape-based single atlas segmentation. The results show segmentation accuracy for each structure in the column, which was segmented by single atlas registration based on manual annotation of the structure listed in each row. See text for more details.

|  | RCO | SDA | trachea | lung | clavicle | average |
|---|---|---|---|---|---|---|
| CA(5) | 0.654 | 0.859 | 0.602 | 0.887 | 0.503 | 0.701 |
| DA(5) | 0.673 | 0.887 | 0.603 | 0.900 | 0.563 | 0.725 |
| CA(10) | 0.728 | 0.895 | 0.668 | 0.913 | 0.631 | 0.767 |
| DA(10) | 0.747 | 0.913 | 0.699 | 0.926 | 0.674 | 0.792 |
| CA(20) | 0.769 | 0.908 | 0.695 | 0.917 | 0.711 | 0.800 |
| DA(20) | 0.781 | 0.939 | 0.747 | 0.948 | 0.783 | 0.840 |

Table 2. Segmentation performance (mean dice similarity coefficient) using centralized and distributed annotation. Number of annotations per structure used in training is given in parentheses.

FIG. 3

REDUCING STRUCTURAL REDUNDANCY IN AUTOMATIC IMAGE SEGMENTATION

BACKGROUND

The present invention relates generally to the field of computing, and more specifically, to a distributed annotation scheme to reduce structural redundancy in digital image processing and segmentation.

Generally, in digital image processing and computer vision, image segmentation is the process of partitioning a digital image into multiple segments (sets of pixels, also known as image objects). The goal of segmentation is to simplify and/or change the representation of an image into something that is more meaningful and easier to analyze. In medical imaging, these segments often correspond to different anatomical structures such as tissue classes, organs, pathologies, or other biologically relevant structures. For many applications, a medical expert may manually label several images. But with recent technological advancements, automatic segmentation has become a more effective alternative to human annotation in many applications. However, manual annotation may still be necessary for training automatic methods. Specifically, manual segmentation may be essential for building segmentation algorithms and thereby improving automatic segmentation. Generally, some examples of digital image segmentation techniques may include atlas-based segmentation, shape-based segmentation, image-based segmentation, interactive segmentation, and subjective surface segmentation.

SUMMARY

A method for automatically training and applying automatic segmentation in digital image processing is provided. The method may include, in response to receiving a plurality of digital images wherein each digital image associated with the plurality of digital images comprises only one annotated structure out of a plurality of structures included in each digital image, applying a predictive algorithm to each digital image that determines a predicted probability of each annotation in each digital image, determines a predicted background for each digital image, and merges the predicted probability of each annotation with the predicted background in each digital image. The method may further include, in response to applying the predictive algorithm, using the received plurality of digital images to train and apply an application for automatically segmenting unlabeled digital images.

A computer system for automatically training and applying automatic segmentation in digital image processing is provided. The computer system may include one or more processors, one or more computer-readable memories, one or more computer-readable tangible storage devices, and program instructions stored on at least one of the one or more storage devices for execution by at least one of the one or more processors via at least one of the one or more memories, whereby the computer system is capable of performing a method. The method may include, in response to receiving a plurality of digital images wherein each digital image associated with the plurality of digital images comprises only one annotated structure out of a plurality of structures included in each digital image, applying a predictive algorithm to each digital image that determines a predicted probability of each annotation in each digital image, determines a predicted background for each digital image, and merges the predicted probability of each annotation with the predicted background in each digital image. The method may further include, in response to applying the predictive algorithm, using the received plurality of digital images to train and apply an application for automatically segmenting unlabeled digital images.

A computer program product for automatically training and applying automatic segmentation in digital image processing is provided. The computer program product may include one or more computer-readable storage devices and program instructions stored on at least one of the one or more tangible storage devices, the program instructions executable by a processor. The computer program product may include program instructions to, in response to receiving a plurality of digital images wherein each digital image associated with the plurality of digital images comprises only one annotated structure out of a plurality of structures included in each digital image, apply a predictive algorithm to each digital image that determines a predicted probability of each annotation in each digital image, determines a predicted background for each digital image, and merges the predicted probability of each annotation with the predicted background in each digital image. The computer program product may include program instructions to, in response to applying the predictive algorithm, use the received plurality of digital images to train and apply an application for automatically segmenting unlabeled digital images.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings:

FIG. 3 is an exemplary diagram depicting advantages of distributed annotation in by illustrating testing results based on an application of the distributed annotation scheme associated with a program for automatically training and applying automatic segmentation in digital image processing according to one embodiment;

DETAILED DESCRIPTION

Figure 1:
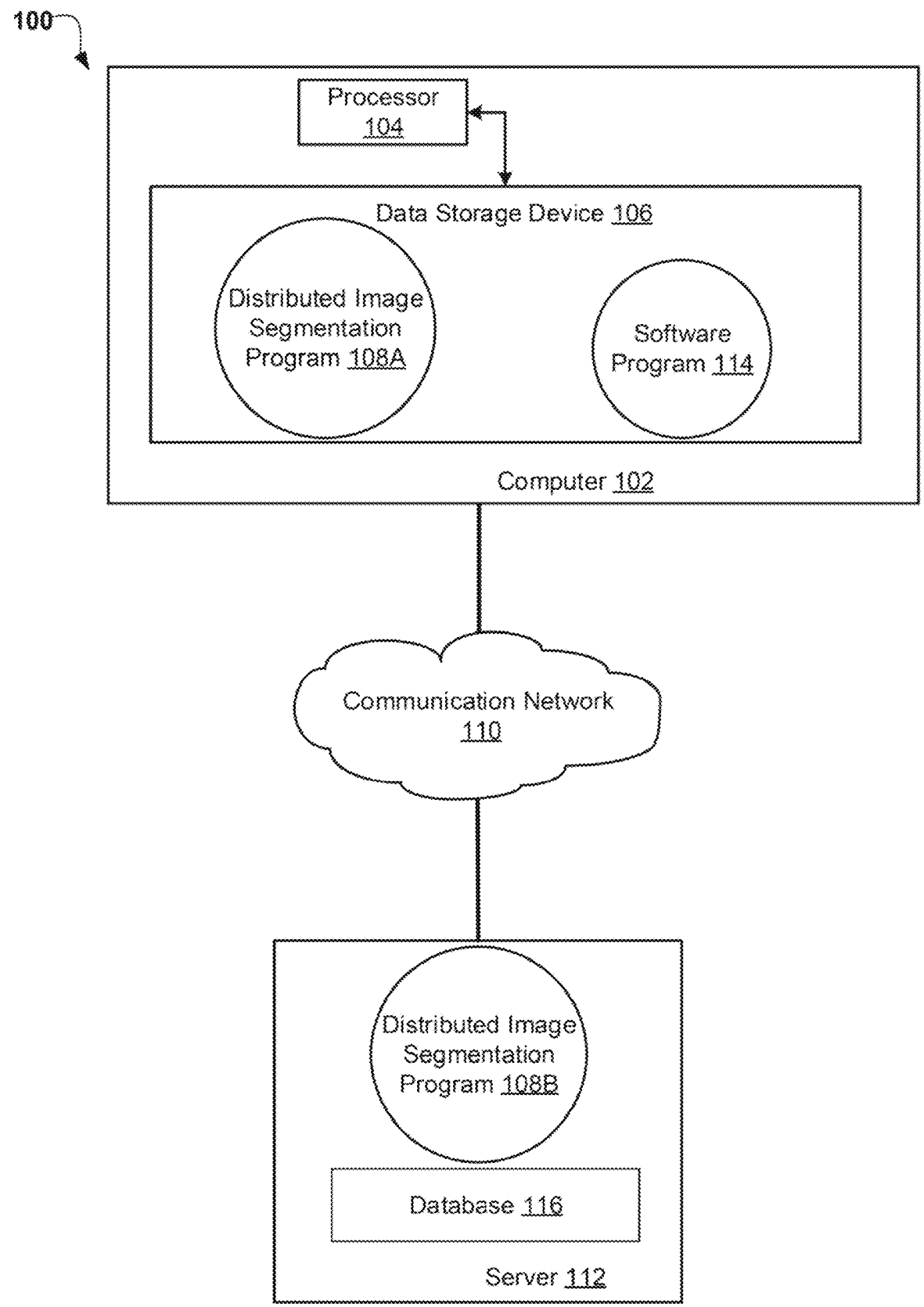
FIG. 1 illustrates a networked computer environment according to one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

Embodiments of the present invention relate generally to the field of computing, and more particularly, to digital image processing and segmentation. The following described exemplary embodiments provide a system, method and program product for automatically training and applying automatic segmentation in digital image processing. Specifically, the present embodiment has the capacity to improve the technical field associated with digital image processing, and particularly digital image segmentation, by reducing structural redundancy in image segmentation. More specifically, the system, method and computer program product may make digital image segmentation more effective based on a distributed annotation strategy to reduce structural redundancy such that only one structure of interest is annotated in each digital image, and with a predictive algorithm applied to each digital image, the digital images may be used for training automatic segmentation. As such, in response to receiving an unlabeled digital image for image segmentation, the system, method and computer program product may use the automatic segmentation module to automatically and fully segment/annotate the unlabeled digital image.

As previously described with respect to medical image segmentation, with recent technological advancements, automatic segmentation has become an effective alternative to human annotation in many applications. Manual annotation may still be may be essential for building segmentation algorithms and improving automatic segmentation techniques. However, at the same time, manual segmentation may be a slow and expensive process. Some techniques have been developed to address this problem, such as semi-supervised learning techniques which have been developed and used to reduce the demand for manual annotation by enabling unlabeled data for automatic learning. In parallel with such efforts, other lines of research have focused more on directly improving the speed and effectiveness of segmentation. Such methods usually achieve more effective segmentation by reducing redundancy in the annotation—in particular, image redundancy and spatial redundancy have been addressed. However, techniques for reducing structural redundancy in medical image segmentation has not been explored.

Therefore, embodiments of the present invention may include a new strategy/process for more effective medical image segmentation by exploring and reducing structural redundancy in medical image segmentation. Typically, in medical image segmentation, when given an image such as an X-ray image, the X-ray image may be fully annotated, i.e. labeled, so that the fully annotated image may be used to help train automatic segmentation methods to recognize each of the structures in the image. However, embodiments of the present invention are based on an observation that anatomical structures are often correlated with each other in that the annotation of just one structure in the image may also render information about other structures in the same image. For example, anatomical structures in medical images usually have relatively constant spatial relations. Thus, knowing where one structure is in a given medical image may also give clues for where other structures are in that same medical image. Due to such structural correlations, annotating multiple structures in one image may be redundant and the fully annotated image may not be properly aligned with a received image. Therefore, to make image segmentation more effective, embodiments of the present invention propose a distributed annotation strategy to reduce structural redundancy such that only one structure of interest is annotated in each digital image for training automatic segmentation. In turn, the segmentation of a single structure in a digital image may be used to predict the segmentation of other structures in other digital images.

As such, it may be advantageous, among other things, to provide a method, computer system, and computer program product for training automatic digital image segmentation using distributed annotation of a digital image to reduce structural redundancy. Specifically, the system, method and computer program product may receive a digital image, such as an X-ray image, that includes multiple structures whereby annotation of the digital image may be distributed across multiple different digital images such that one different structure is annotated in each of the digital images. Thereafter, the system, method and computer program product may apply an algorithm to each of the distributedly annotated digital images that includes one annotated structure to determine and merge a predicted probability of each annotation in the medical image (other than the one annotated structure) with a prediction of background in each of the medical image. Next, the system, method and computer program product may train automatic digital image segmentation by testing and applying the distributed annotation of the medical images.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Referring now to FIG. 1, an exemplary networked computer environment 100 in accordance with one embodiment is depicted. The networked computer environment 100 may include a computer 102 with a processor 104 and a data storage device 106 that is enabled to run a distributed image annotation program 108A and a software program 114 and may also include a microphone (not shown). The software program 114 may be an application program such as an internet browser and/or one or more mobile apps running on a client computer 102, such as a mobile phone device. The distributed image annotation program 108A may communicate with the software program 114. The networked computer environment 100 may also include a server 112 that is enabled to run a distributed image annotation program 108B and the communication network 110. The networked computer environment 100 may include a plurality of computers 102 and servers 112, only one of which is shown for illustrative brevity. For example, the plurality of computers 102 may include a plurality of interconnected devices, such as a mobile phone, tablet, and laptop, associated with one or more users.

According to at least one implementation, the present embodiment may also include a database 116, which may be running on server 112. The communication network 110 may include various types of communication networks, such as a wide area network (WAN), local area network (LAN), a telecommunication network, a wireless network, a public switched network and/or a satellite network. It may be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with server computer 112 via the communications network 110. The communications network 110 may include connections, such as wire, wireless communication links, or fiber optic cables. As will be discussed with reference to FIG. 3, server computer 112 may include internal components 800a and external components 900a, respectively, and client computer 102 may include internal components 800b and external components 900b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a medical device, a mobile device, a telephone, a personal digital assistant, a netbook, a laptop computer, a tablet computer, a desktop computer, or any type of computing device capable of running a program and accessing a network. According to various implementations of the present embodiment, the distributed image annotation program 108A, 108B may interact with a database 116 that may be embedded in various storage devices, such as, but not limited to, a mobile device 102, a networked server 112, or a cloud storage service.

According to the present embodiment, a program, such as a distributed image annotation program 108A and 108B may run on the client computer 102 and/or on the server computer 112 via a communications network 110. The distributed image annotation program 108A, 108B may train and apply automatic image segmentation methods based on distributed annotation of a digital image. Specifically, a user using a client computer 102, such as a medical device, may run a distributed image annotation program 108A, 108B, that may interact with a database 116 and a software program 114, such as medical image processing application and/or a web browser, to receive a digital image, such as a digital X-ray image, that includes multiple structures whereby annotation of the digital image may be distributed across multiple copies of the digital image such that one different structure is annotated in each copy of the digital image. Thereafter, the distributed image annotation program 108A, 108B may dynamically apply an algorithm to each of the digital images that include one annotated structure to determine a predicted probability of each annotation in the digital image (i.e. predicting the annotation of other structures in a digital image other than the one annotated structure), determine a predicted background for each digital image, and merge the predicted probability of each annotation with the predicted background. Subsequently, the distributed image annotation program 108A, 108B may train and apply automatic image segmentation using a collection of the digital images that include one annotated structure.

Figure 2:
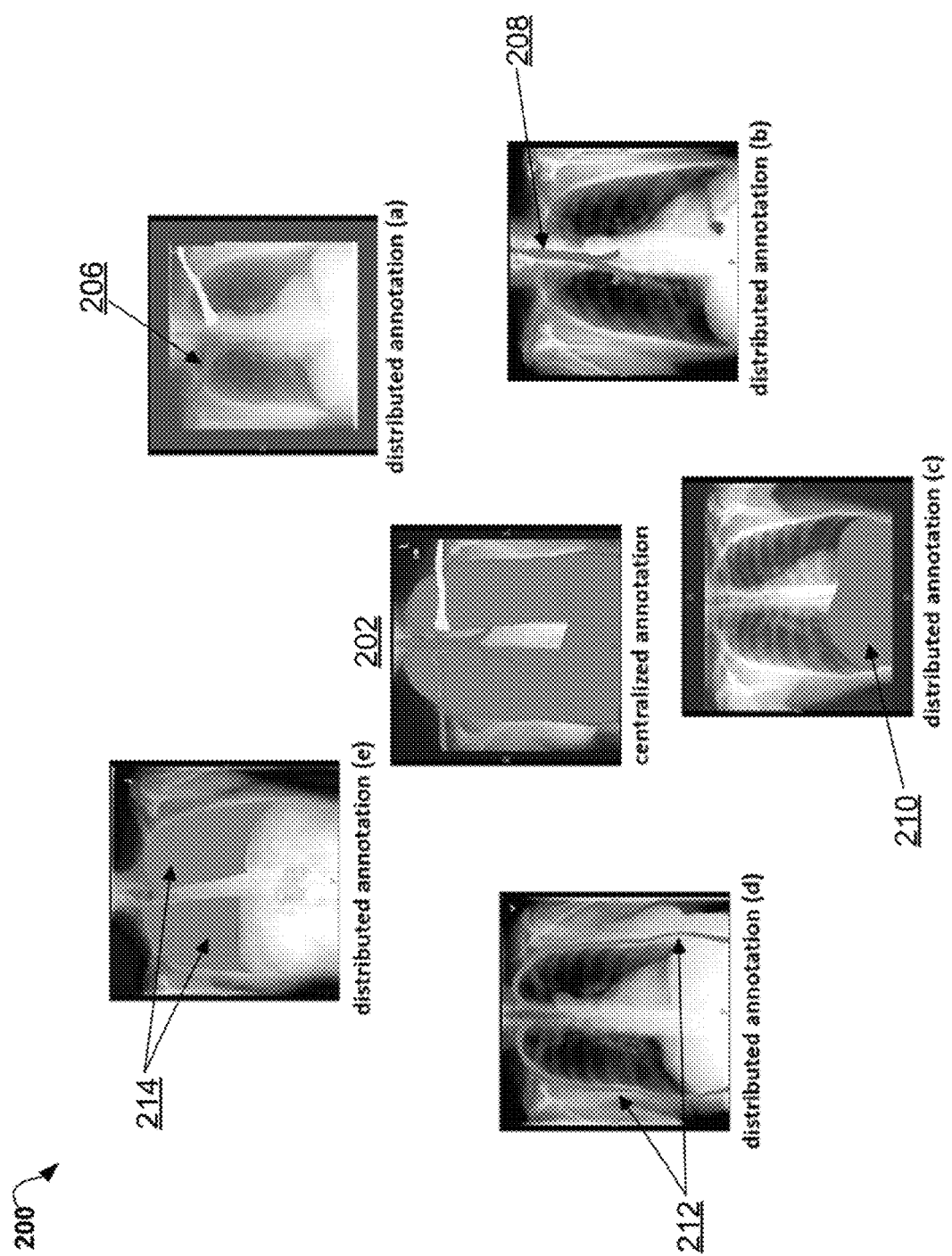
FIG. 2 is a block diagram illustrating centralized annotation versus the distributed annotation scheme associated with a program for automatically training and applying automatic segmentation in digital image processing according to one embodiment.

Referring now to FIG. 2, a block diagram 200 illustrating centralized annotation versus the distributed annotation scheme associated with the distributed image annotation program 108A (FIG. 1) according to one embodiment is depicted. As previously described with respect to digital medical images, typically in digital image segmentation, a digital medical image such as an X-ray image 202 may be fully annotated such that each structure in the X-ray image 202 is labeled based on a process that may be referred to as centralized annotation 204. However, the distributed image annotation program 108A (FIG. 1) is based on an observation that anatomical structures in medical images are often correlated with each other in that the annotation of just one structure in the image may also render information about other structures. For example, anatomical structures in a digital medical image associated with the human body usually has relatively constant spatial relations. Therefore, knowing where one structure is in a given X-ray image 202 may also give clues for where other structures may be located. Due to such structural correlations, annotating multiple structures in one image may be redundant for automatically annotating the other given image.

As depicted in FIG. 2, the X-ray image 202 in the center is an example of centralized annotation, where all structures are annotated in the training X-ray image. However, using the proposed distributed annotation scheme associated with the distributed image annotation program 108A (FIG. 1) that is illustrated in the surrounding images, annotations are distributed across more images where only one structure is annotated in each X-ray image. Specifically, the annotated structures include (a) clavicle 206, (b) trachea 208, (c) sub diaphragmatic area 210, (d) rib cage outline 212, and (e) lung 214.

FIG. 3 further depicts advantages of distributed annotation in Tables 302 and 304 by illustrating testing results based on application of the distributed annotation scheme associated with the distributed image annotation program 108A, 108B (FIG. 1). Specifically, as depicted in Table 1 (at 302), to demonstrate the structural correlation between structures in a digital X-ray image, shape-based single atlas segmentation was used in a cross-validation test where each image was applied as an atlas once to segment the remaining training images. More specifically, and as depicted in Table 1 (at 302) of FIG. 3, the left column represents fully annotated digital images (atlas image), and the top row represents the digital images where only one structure is annotated (target image). For testing the accuracy of distributed annotation using shape-based single atlas segmentation, one structure in the fully annotated images were aligned with the only annotated structure in the digital images that included just the one annotated structure (in the top row) to determine whether that alignment accurately predicts (or annotates) the remaining structures in the digital image that contains just the one annotated structure. For example, as depicted in row 1 of Table 1 (at 302), the rib cage outline (RCO) from the fully annotated digital image was aligned with the digital image that included just the annotated RCO to predict the other 4 structures in the digital image that included just the annotated RCO. Thereafter, the prediction of the full annotation of the digital image that included just the annotated rib cage outline was tested against a full manual annotation of the digital image that included just the annotated rib cage outline (i.e. the digital image that included just the annotated rib cage outline was fully annotated manually and compared to the prediction). Thus, when one structure was applied for segmentation, affine registration between an atlas and a target image was computed based on the related annotated structures in both images. Based on the registration, the segmentation of the remaining structures was propagated from the atlas to the target image. Since this segmentation method only relies on spatial relations among the structures in the atlas for segmentation, this test captures shape-based structural correlation. Table 1 (at 302) in FIG. 3 summarizes an average segmentation accuracy using Dice similarity coefficient, whereby each number represents a level of accuracy for predicting the remaining structures in each digital image. Specifically, in Table 1 (at 302), the higher the number the better the prediction. This result shows that each structure contains information for segmenting other structures. In particular, for example, the lung produced the best and the sub diaphragmatic area (i.e. SDA) produced the worst shape-based segmentation accuracy for other structures, respectively. As noted, the lung structure is located in the middle and is the closest to all structures, however the sub diaphragmatic area is the only structure located in the bottom region and is the farthest from other structures. Such results depict that shape-based structural correlation is stronger for spatially closer structures.

Table 2 (at 304) in FIG. 3, further depicts differences and advantages of distributed annotation by comparing testing results associated with centralized annotation (CA) with the proposed distributed annotation scheme (DA), where annotations produced by the two methods under similar annotation efforts were applied to train and test segmentation models. Specifically, 150 digital X-ray images were used as data where each of the digital images include 5 structures that are fully annotated. Among the 150 digital X-ray images, 100 were randomly selected and used for training, 25 were randomly selected for validation, and the remaining 25 were used only for testing purpose. The performance on the testing data gives a quantitative comparison between the two annotation strategies (i.e. centralized annotation and distributed annotation). In Table 2 (at 304), to compare different levels of annotation efforts, the tested number of annotations per structure was varied among 5, 10, and 20. Since each of the 100 digital images were fully annotated, for a test with N annotations per structure, N images were randomly chosen from the 100 digital images for centralized annotation. For example, for 5 annotations per structure, 5 images were randomly chosen for centralized annotation since centralized annotations requires fully annotated images. However, to use one of the digital images in distributed annotation, all but one annotated structure is removed in the digital image. Thus, for distributed annotation, out of the 100 digital images, 5 non-overlapping sets of images for the 5 structures were chosen (i.e. 5 images where RCO is the only structure annotated, 5 images where SDA is the only structure annotated, 5 images where trachea is the only structure annotated, 5 images where lung is the only structure annotated, and 5 images where clavicle is the only structure annotated), which essentially included a total of 25 images. Thus, for example, in Table 2, CA(5) stands for 5 fully annotated training images and DA(5) stands for 25 training images but each with only one structure annotated, CA(10) stands for 10 fully annotated training images and DA(10) stands for 50 training images but each with only one structure annotated, and CA(20) stands for 20 fully annotated training images and DA(20) stands for 100 training images but each with only one structure annotated.

For evaluating the performance of the trained automatic segmentation algorithm, the trained algorithm was applied to predict segmentations for the testing images. As previously described, the testing images are fully annotated digital images. The performance was then measured between the predicted segmentation and the annotated segmentation. Table 2 (at 304) in FIG. 3 summarizes an average segmentation accuracy (based on Dice similarity coefficient) that was produced using centralized annotation and distributed annotation, respectively, where distributed annotation outperforms centralized annotation. Specifically, each number represents a level of accuracy associated with the collection of digital images from the respective methods (left column) for predicting the remaining structures in each digital image containing only one annotated structure (the top row).

Figure 4:
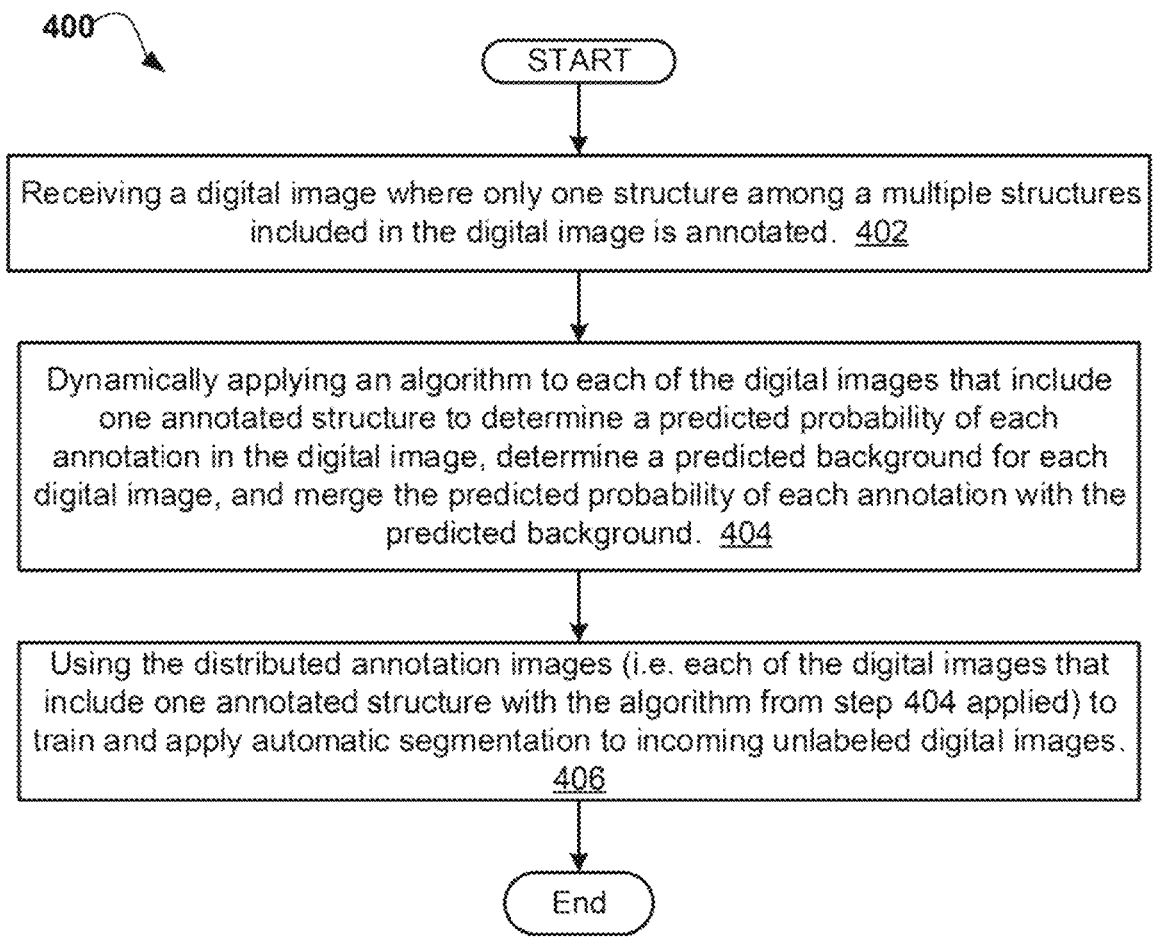
FIG. 4 is an operational flowchart illustrating the steps carried out by a program for automatically training and applying automatic segmentation in digital image processing according to one embodiment.

Referring now to FIG. 4, an operational flowchart 400 illustrating the steps carried out by a program for training automatic segmentation using the distributed annotation process according to one embodiment is depicted. Specifically, at 402, the distributed image annotation program 108A (FIG. 1) may receive a digital image, such as an X-ray image, where only one structure among multiple structures included in the digital image is annotated in the digital image. According to one embodiment, the distributed image annotation program 108A (FIG. 1) may include a user interface for presenting a digital image to a user such as a medical expert and/or doctor. For example, for an X-ray image with N structures of interest for annotating, the distributed image annotation program 108A (FIG. 1) may present N times images for annotation. More specifically, for example, the distributed image annotation program 108A (FIG. 1) may use machine learning computer vision technology to determine that a digital chest X-ray image may have 5 structures of interest for annotating—clavicle, trachea, sub diaphragmatic area, rib cage outline, and lung. Therefore, the distributed image annotation program 108A (FIG. 1) may present 5 different digital chest X-ray images to the user and prompt the user to provide an annotation of one structure in each image. As such, the distributed image annotation program 108A (FIG. 1) may receive a first digital image where the clavicle 206 (FIG. 2) is the only structure annotated, a second digital image where the trachea 208 (FIG. 2) is the only structure annotated, a third digital image where the sub diaphragmatic area 210 (FIG. 2) is the only structure annotated, a fourth digital image where the rib cage outline 212 (FIG. 2) is the only structure annotated, and a fifth digital image where the lung 214 (FIG. 2) is the only structure annotated.

According to one embodiment, it is not necessary for the distributed image annotation program 108A (FIG. 1) to receive an annotation for each structure for one digital image. Specifically, according to one embodiment, the distributed image annotation program 108A (FIG. 1) may present the digital X-ray image once or multiple times and still prompt the user to annotate one structure in the digital X-ray image. For example, for the chest X-ray depicted in FIG. 2, the distributed image annotation program 108A (FIG. 1) may present and then receive a copy of the image where the trachea 208 is the only structure annotated based on user feedback and also another copy of the image where the sub diaphragmatic area 210 is the only structure annotated based on user feedback. However, from a different chest X-ray image, the distributed image annotation program 108A (FIG. 1) may present and receive a copy of the different chest X-ray image where just the rib cage outline 212 is the only structure annotated. Thus, according to one embodiment, the distributed image annotation program 108A (FIG. 1) may include a database 116 (FIG. 1) of different digital images where only one structure is annotated in each of the different images.

Thereafter, at 404, the distributed image annotation program 108A, 108B may dynamically apply a predictive algorithm to each of the digital images that include one annotated structure to determine a predicted probability of each annotation in the digital image (i.e. predicting the annotation of other structures other than the one annotated structure), determine a predicted background for each digital image, and merge the predicted probability of each annotation with the predicted background. As previously described at step 402, in distributed annotation, different training images may have different structures annotated. With each annotation, the background portions of a digital image may mistakenly include some non-background structures, or more specifically, other non-annotated structures in the image may be mistaken as the background. Without correcting such information, each of the medical images with only one structure annotated may not be properly applied for training automatic segmentation (and specifically a learning model associated with automatic segmentation). For example, if both structures A and B appear in one digital X-ray image but only A is annotated, then there is no uncertain region for structure A. However, for structure B, the uncertain region is the rest of the entire image (i.e. excluding the annotated A region) because the rest of the entire image may belong to either the actual background or to the structure B. Thus, although the digital image can be used by distributed annotation, it may not fully provide training data as significant imaging data may be excluded from being used in training. Therefore, the distributed image annotation program 108A, 108B may dynamically apply a predictive algorithm to each of the digital medical images that include just one annotated structure to determine a predicted probability of each annotation in the digital image (i.e. predicting the annotation of other structures other than the one annotated structure), determine a predicted background for each digital image, and merge the predicted probability of each annotation with the predicted background.

More specifically, according to one embodiment, to determine the predicted probability of each annotation in the digital image and a predicted background for each digital image, as well as merge the predicted probability with the predicted background, the distributed image annotation program 108A, 108B may use the following predictive algorithm:

$$O(M_\theta(I), S) = \sum_{S(z)=l_I} -\log(p_{l_I}(x \mid I, \theta)) + \sum_{S(z)=0} -\log\left[\sum_{l \neq l_I} p_l(x \mid I, \theta)\right]$$

where $\theta$ represents the parameters of a convolutional neural network that produces segmentation that includes a fully annotated set, $M_\theta(I)$ may be the result produced by a model for image I,
S may be manual segmentation for I,
$l_I$ is the only non-background structure annotated in S,
x is an index through image voxels, $p_l$ is the model predicted probability for label l, and l=0 is the background annotation. Since only $l_I$ is annotated for I and all other structures are annotated as background, to make the predicted background comparable to the one annotation, $\Sigma_{l \neq l_I} p_l(x \mid I, \theta)$ merges the predicted probability for every annotation other than lI with the prediction of the background. Therefore, even though a background region may at first be uncertain based on any single annotation of a structure in a digital image (where the digital image includes multiple structures), the uncertainty may be removed using the above algorithm to determine and merge the predicted probability of each annotation in the digital image with the prediction of the background in the digital image. In turn, the distributed image annotation program 108A, 108B may use the algorithm to prevent background and structurally relevant regions in a given digital image from being excluded when using the digital image to train automatic segmentation.

Thereafter, the distributed image annotation program 108A, 108B may use the distributed annotation images (i.e. each of the digital images that include one annotated structure with the predictive algorithm from step 404 applied to the digital image) to train and apply automatic segmentation to incoming, unlabeled digital images. Specifically, the distributed image annotation program 108A, 108B may include an automatic segmentation module, whereby the automatic segmentation module may include a machine learning computer vision algorithm as well as include a collection of the digital images that have just one structure annotated in each of the digital images. Furthermore, with the predictive algorithm from step 404 having been applied to each of the digital images in the collection of digital images, the distributed image annotation program 108A, 108B may use the digital images and the machine learning computer vision algorithm to train the automatic segmentation module to detect and label (i.e. segment/annotate) structures in an unlabeled digital image that is presented for image segmentation. According to one embodiment, the machine learning computer vision algorithm may be a combination of computer vision technology as well as image segmentation techniques such as atlas-based segmentation, shape-based segmentation, image-based segmentation, interactive segmentation, and subjective surface segmentation. As such, in response to receiving an unlabeled digital image for image segmentation, the distributed image annotation program 108A, 108B may use the automatic segmentation module to automatically and fully segment/annotate the unlabeled digital image (i.e. identify the anatomical structures within the unlabeled digital image) based on the collection of the digital images that have just one structure annotated with the predictive algorithm from step 404 having been applied to each of the digital images. Accordingly, the distributed image annotation program 108A, 108B may include a second user interface for receiving unlabeled digital images and for applying the trained automatic segmentation module to the received unlabeled digital images.

It may be appreciated that FIGS. 1-4 provide only illustrations of one implementation and does not imply any limitations with regard to how different embodiments may be implemented. Many modifications to the depicted environments may be made based on design and implementation requirements.

The present invention may be a system, a method, and/or a computer program product. The computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 5:
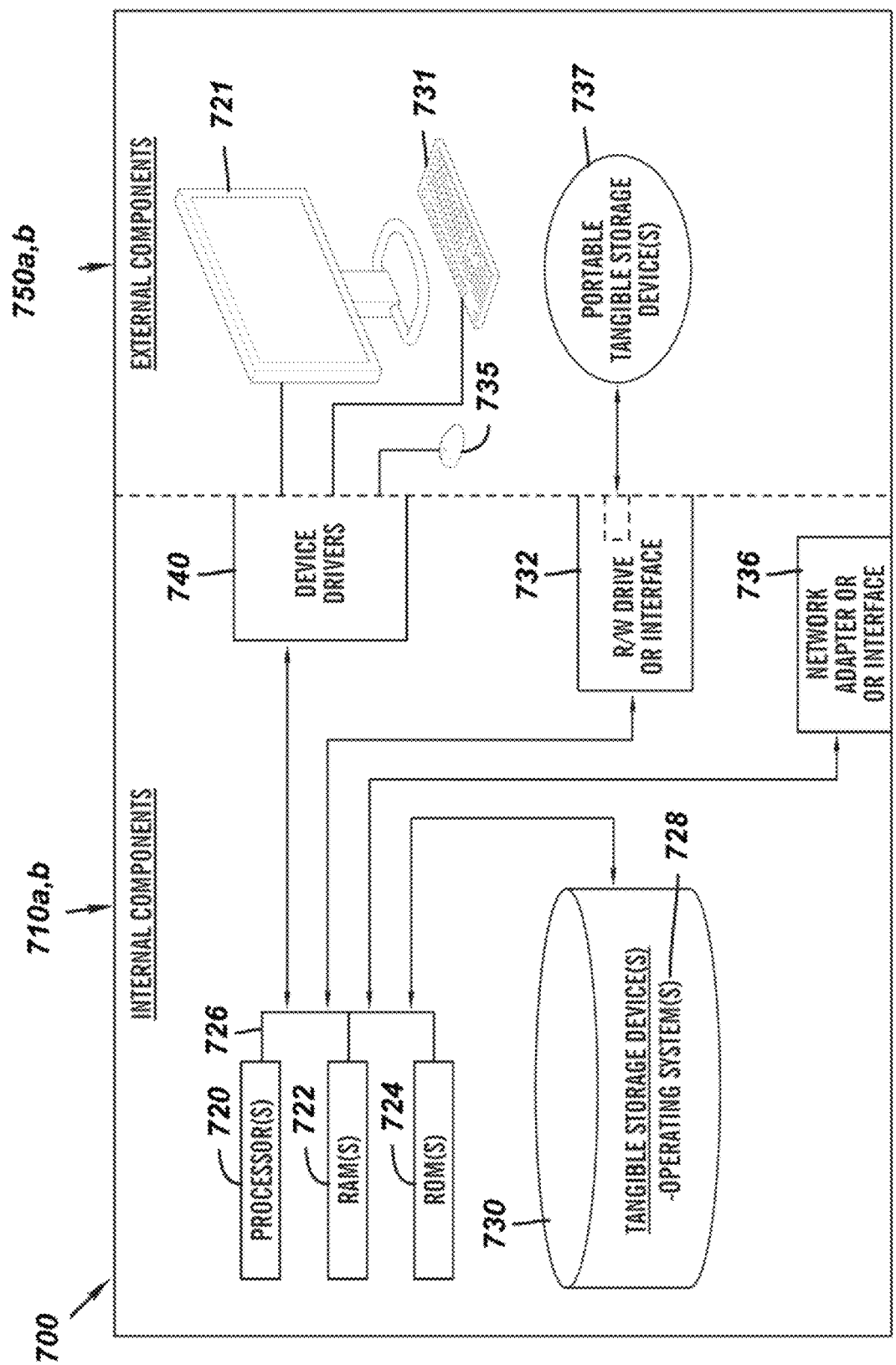
FIG. 5 is a block diagram of the system architecture of the program for automatically training and applying automatic segmentation in digital image processing according to one embodiment.

FIG. 5 is a block diagram 700 of internal and external components of computers depicted in FIG. 1 in accordance with an illustrative embodiment of the present invention. It should be appreciated that FIG. 5 provides only an illustration of one implementation and does not imply any limitations with regard to the environments in which different embodiments may be implemented. Many modifications to the depicted environments may be made based on design and implementation requirements.

Data processing system 710, 750 is representative of any electronic device capable of executing machine-readable program instructions. Data processing system 710, 750 may be representative of a smart phone, a computer system, PDA, or other electronic devices. Examples of computing systems, environments, and/or configurations that may be represented by data processing system 710, 750 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 (FIG. 1), and network server 112 (FIG. 1) include respective sets of internal components 710 *a, b* and external components 750 *a, b* illustrated in FIG. 5. Each of the sets of internal components 710 *a, b* includes one or more processors 720, one or more computer-readable RAMs 722, and one or more computer-readable ROMs 724 on one or more buses 726, and one or more operating systems 728 and one or more computer-readable tangible storage devices 730. The one or more operating systems 728, the software program 114 (FIG. 1) and the distributed image annotation program 108A (FIG. 1) in client computer 102

(FIG. 1), and the distributed image annotation program 108B (FIG. 1) in network server computer 112 (FIG. 1) are stored on one or more of the respective computer-readable tangible storage devices 730 for execution by one or more of the respective processors 720 via one or more of the respective RAMs 722 (which typically include cache memory). In the embodiment illustrated in FIG. 5, each of the computer-readable tangible storage devices 730 is a magnetic disk storage device of an internal hard drive. Alternatively, each of the computer-readable tangible storage devices 730 is a semiconductor storage device such as ROM 724, EPROM, flash memory or any other computer-readable tangible storage device that can store a computer program and digital information.

Each set of internal components 710 a, b, also includes a RAY drive or interface 732 to read from and write to one or more portable computer-readable tangible storage devices 737 such as a CD-ROM, DVD, memory stick, magnetic tape, magnetic disk, optical disk or semiconductor storage device. A software program, such as a distributed image annotation program 108A and 108B (FIG. 1), can be stored on one or more of the respective portable computer-readable tangible storage devices 737, read via the respective RAY drive or interface 732, and loaded into the respective hard drive 730.

Each set of internal components 710 a, b also includes network adapters or interfaces 736 such as a TCP/IP adapter cards, wireless Wi-Fi interface cards, or 3G or 4G wireless interface cards or other wired or wireless communication links. The distributed image annotation program 108A (FIG. 1) and software program 114 (FIG. 1) in client computer 102 (FIG. 1), and the distributed image annotation program 108B (FIG. 1) in network server 112 (FIG. 1) can be downloaded to client computer 102 (FIG. 1) from an external computer via a network (for example, the Internet, a local area network or other, wide area network) and respective network adapters or interfaces 736. From the network adapters or interfaces 736, the distributed image annotation program 108A (FIG. 1) and software program 114 (FIG. 1) in client computer 102 (FIG. 1) and the distributed image annotation program 108B (FIG. 1) in network server computer 112 (FIG. 1) are loaded into the respective hard drive 730. The network may comprise copper wires, optical fibers, wireless transmission, routers, firewalls, switches, gateway computers, and/or edge servers.

Each of the sets of external components 750 a, b can include a computer display monitor 721, a keyboard 731, and a computer mouse 735. External components 750 a, b can also include touch screens, virtual keyboards, touch pads, pointing devices, and other human interface devices. Each of the sets of internal components 710 a, b also includes device drivers 740 to interface to computer display monitor 721, keyboard 731, and computer mouse 735. The device drivers 740, R/W drive or interface 732, and network adapter or interface 736 comprise hardware and software (stored in storage device 730 and/or ROM 724).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
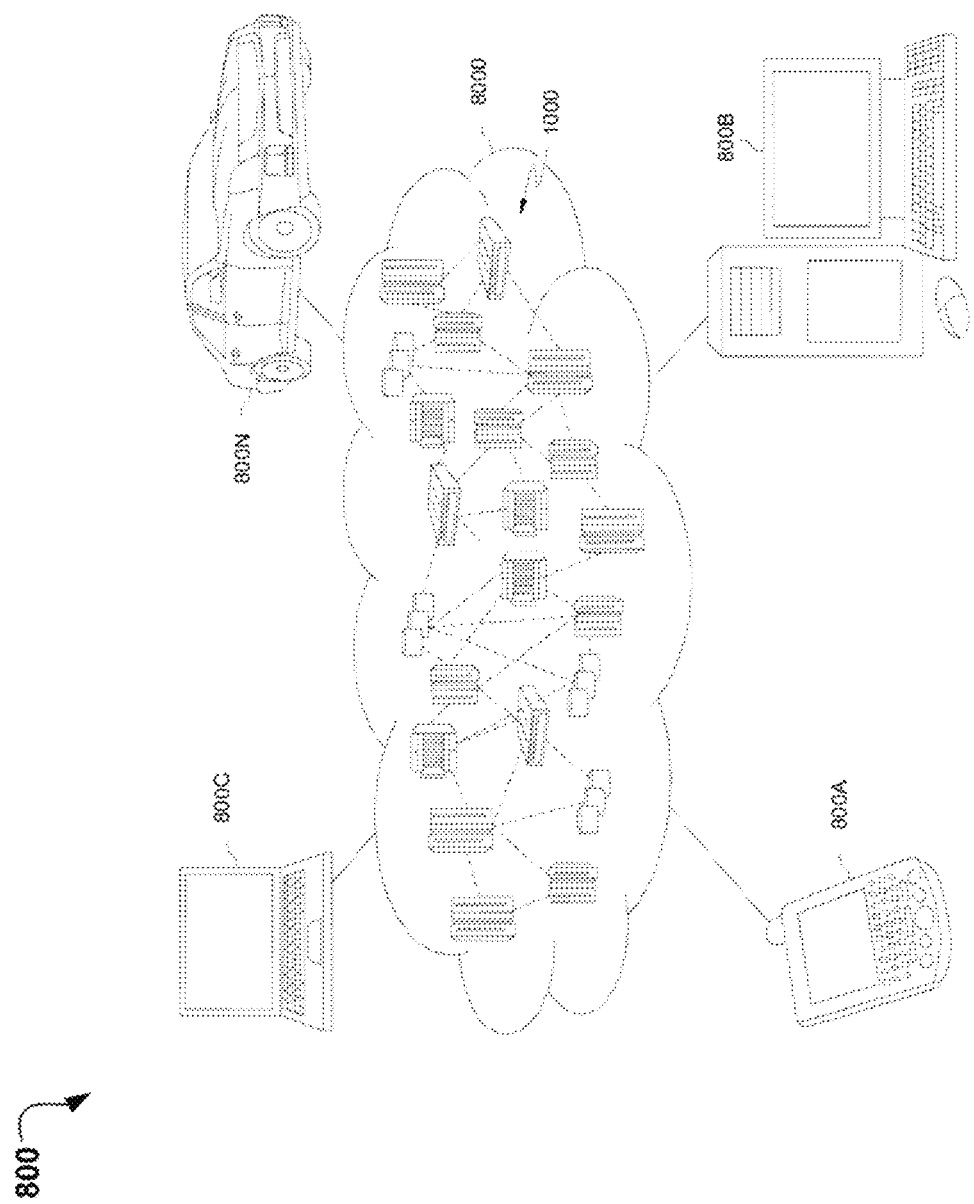
FIG. 6 is a block diagram of an illustrative cloud computing environment including the computer system depicted in FIG. 1, in accordance with an embodiment of the present disclosure.

Referring now to FIG. 6, illustrative cloud computing environment 800 is depicted. As shown, cloud computing environment 800 comprises one or more cloud computing nodes 1000 with which local computing devices used by cloud consumers, such as, for example, personal digital assistant (PDA) or cellular telephone 800A, desktop computer 800B, laptop computer 800C, and/or automobile computer system 800N may communicate. Nodes 1000 may communicate with one another. They may be grouped (not shown) physically or virtually, in one or more networks, such as Private, Community, Public, or Hybrid clouds as described hereinabove, or a combination thereof. This allows cloud computing environment 8000 to offer infrastructure, platforms and/or software as services for which a cloud consumer does not need to maintain resources on a local computing device. It is understood that the types of computing devices 800A-N shown in FIG. 8 are intended to be illustrative only and that computing nodes 100 and cloud computing environment 8000 can communicate with any type of computerized device over any type of network and/or network addressable connection (e.g., using a web browser).

Figure 7:
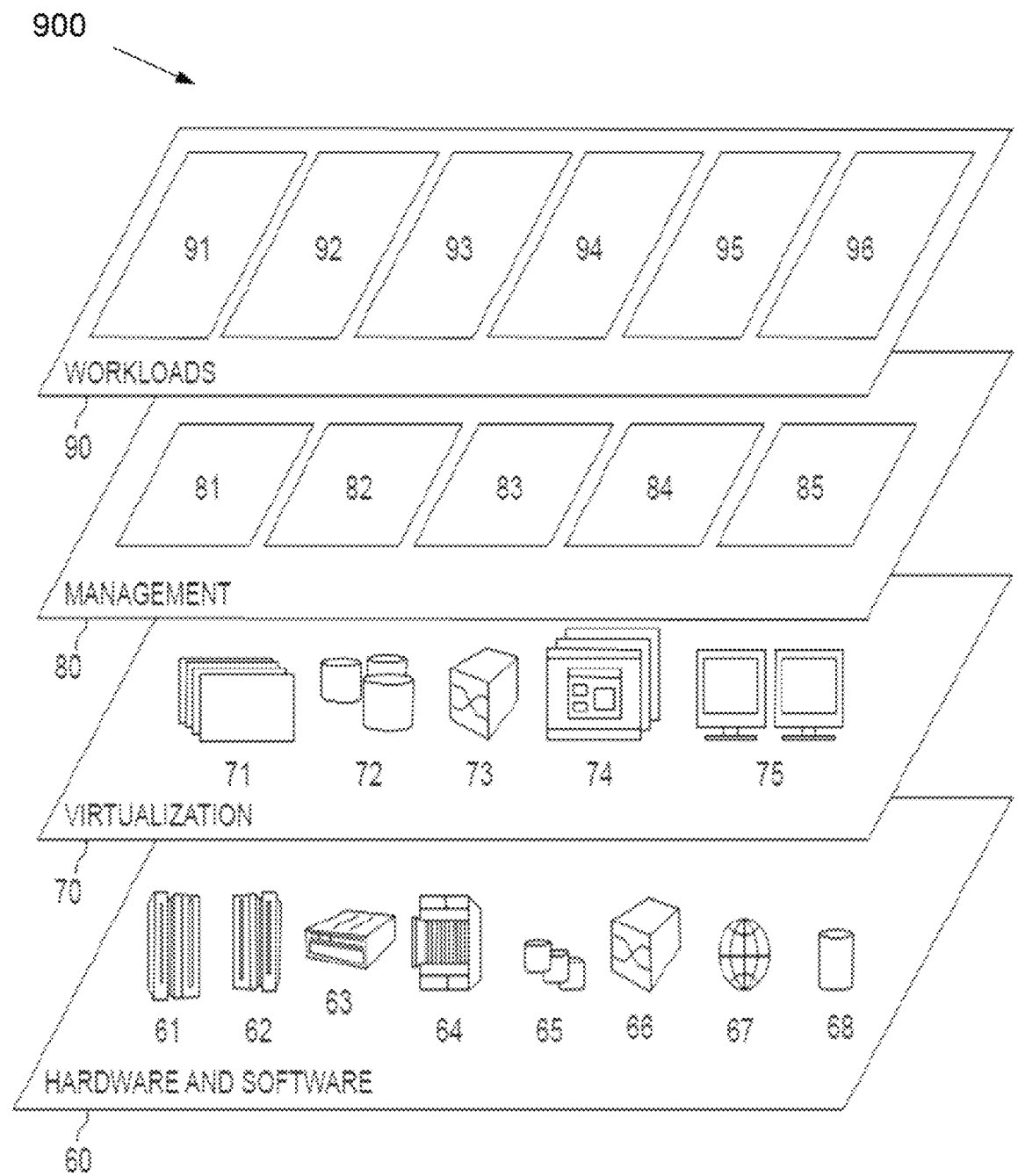
FIG. 7 is a block diagram of functional layers of the illustrative cloud computing environment of FIG. 6, in accordance with an embodiment of the present disclosure.

Referring now to FIG. 7, a set of functional abstraction layers 900 provided by cloud computing environment 800 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and distributed image annotation 96. A distributed image annotation program 108A, 108B (FIG. 1) may be offered "as a service in the cloud" (i.e., Software as a Service (SaaS)) for applications running on computing devices 102 (FIG. 1) and may automatically train and apply automatic segmentation in digital image processing.

The descriptions of the various embodiments of the present invention have been presented for purposes of illustration but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for automatically training and applying automatic segmentation in digital image processing, the method comprising:

in response to receiving a plurality of digital images wherein each digital image associated with the plurality of digital images comprises only one annotated structure out of a plurality of different structures included in each digital image, applying a predictive algorithm to each digital image that determines a predicted probability of annotations for each structure other than the one annotated structure in each digital image based on a spatial and structural correlation of the one annotated structure relative to the plurality of different structures, determines a predicted background for each digital image, and merges the predicted probability of the annotations with the predicted background in each digital image; and in response to applying the predictive algorithm, using the received plurality of digital images to train and apply an application for automatically segmenting unlabeled digital images.

2. The method of claim 1, further comprising:
presenting a user interface and prompting a user to annotate a digital image associated with the plurality of digital images using the user interface.

3. The method of claim 2, wherein presenting the user interface and prompting the user further comprises:
for a digital image with a number of structures of interest for annotating, presenting the same number of different digital images to the user on the user interface and prompting the user to annotate one different structure in each of the different digital images.

4. The method of claim 1, wherein applying the application for automatically segmenting the unlabeled digital images further comprises:
applying a machine learning computer vision algorithm and the received plurality of digital images to the unlabeled digital images to segment the unlabeled digital images.

5. The method of claim 1, wherein the plurality of digital images comprises digital X-ray images.

6. The method of claim 1, wherein automatically segmenting the unlabeled digital images further comprises:
automatically identifying anatomical structures within an unlabeled digital X-ray image.

7. The method of claim 1, wherein the application for automatically segmenting unlabeled digital images includes one or more image segmentation techniques selected from a group comprising at least one of atlas-based segmentation, shape-based segmentation, image-based segmentation, interactive segmentation, and subjective surface segmentation.

8. A computer system for automatically training and applying automatic segmentation in digital image processing, comprising:
one or more processors, one or more computer-readable memories, one or more computer-readable tangible storage devices, and program instructions stored on at least one of the one or more storage devices for execution by at least one of the one or more processors via at least one of the one or more memories, wherein the computer system is capable of performing a method comprising:
in response to receiving a plurality of digital images wherein each digital image associated with the plurality of digital images comprises only one annotated structure out of a plurality of different structures included in each digital image, applying a predictive algorithm to each digital image that determines a predicted probability of annotations for each structure other than the one annotated structure in each digital image based on a spatial and structural correlation of the one annotated structure relative to the plurality of different structures, determines a predicted background for each digital image, and merges the predicted probability of the annotations with the predicted background in each digital image; and
in response to applying the predictive algorithm, using the received plurality of digital images to train and apply an application for automatically segmenting unlabeled digital images.

9. The computer system of claim 8, further comprising:
presenting a user interface and prompting a user to annotate a digital image associated with the plurality of digital images using the user interface.

10. The computer system of claim 9, wherein presenting the user interface and prompting the user further comprises:
for a digital image with a number of structures of interest for annotating, presenting the same number of different digital images to the user on the user interface and prompting the user to annotate one different structure in each of the different digital images.

11. The computer system of claim 8, wherein applying the application for automatically segmenting the unlabeled digital images further comprises:
applying a machine learning computer vision algorithm and the received plurality of digital images to the unlabeled digital images to segment the unlabeled digital images.

12. The computer system of claim 8, wherein the plurality of digital images comprises digital X-ray images.

13. The computer system of claim 8, wherein automatically segmenting the unlabeled digital images further comprises:
automatically identifying anatomical structures within an unlabeled digital X-ray image.

14. The computer system of claim 8, wherein the application for automatically segmenting unlabeled digital images includes one or more image segmentation techniques selected from a group comprising at least one of atlas-based segmentation, shape-based segmentation, image-based segmentation, interactive segmentation, and subjective surface segmentation.

15. A computer program product for automatically training and applying automatic segmentation in digital image processing, comprising:
one or more tangible computer-readable storage devices and program instructions stored on at least one of the one or more tangible computer-readable storage devices, the program instructions executable by a processor, the program instructions comprising:
in response to receiving a plurality of digital images wherein each digital image associated with the plurality of digital images comprises only one annotated structure out of a plurality of different structures included in each digital image, program instructions to apply a predictive algorithm to each digital image that determines a predicted probability of annotations for each structure other than the one annotated structure in each digital image based on a spatial and structural correlation of the one annotated structure relative to the plurality of different structures, determines a predicted background for each digital image, and merges the predicted probability of the annotations with the predicted background in each digital image; and
in response to applying the predictive algorithm, program instructions to use the received plurality of digital images to train and apply an application for automatically segmenting unlabeled digital images.

16. The computer program product of claim 15, further comprising:
program instructions to present a user interface and prompt a user to annotate a digital image associated with the plurality of digital images using the user interface.

17. The computer program product of claim 16, wherein the program instructions to present the user interface and prompt the user further comprises:
program instructions to, for a digital image with a number of structures of interest for annotating, presenting the same number of different digital images to the user on the user interface and prompting the user to annotate one different structure in each of the different digital images.

18. The computer program product of claim 15, wherein the program instructions to apply the application for automatically segmenting the unlabeled digital images further comprises:
program instructions to apply a machine learning computer vision algorithm and the received plurality of digital images to the unlabeled digital images to segment the unlabeled digital images.

19. The computer program product of claim 15, wherein the program instructions to automatically segment the unlabeled digital images further comprises:
automatically identifying anatomical structures within an unlabeled digital X-ray image.

20. The computer program product of claim 15, wherein the application for automatically segmenting unlabeled digital images includes one or more image segmentation techniques selected from a group comprising at least one of atlas-based segmentation, shape-based segmentation, image-based segmentation, interactive segmentation, and subjective surface segmentation.

* * * * *